US012781187B2

(12) United States Patent
Zhu et al.

(10) Patent No.: US 12,781,187 B2
(45) Date of Patent: Nov. 3, 2026

(54) METHODS FOR PREPARING ENGINEERED MICROVESSELS AND APPLICATIONS THEREOF

(71) Applicant: ARMY MEDICAL UNIVERSITY, Chongqing (CN)

(72) Inventors: Chuhong Zhu, Chongqing (CN); Ming Ke, Chongqing (CN)

(73) Assignee: ARMY MEDICAL UNIVERSITY, Chongqing (CN)

( * ) Notice: Subject to any disclaimer, the term of this patent is extended or adjusted under 35 U.S.C. 154(b) by 0 days.

(21) Appl. No.: 18/915,348

(22) Filed: Oct. 14, 2024

(65) Prior Publication Data

US 2025/0034526 A1 Jan. 30, 2025

Related U.S. Application Data

(63) Continuation of application No. PCT/CN2023/080957, filed on Mar. 11, 2023.

(30) Foreign Application Priority Data

Jan. 29, 2023 (CN) ......................... 202310044224.1

(51) Int. Cl.
*C12N 5/071* (2010.01)
*C12N 5/077* (2010.01)

(52) U.S. Cl.
CPC ........... *C12N 5/0657* (2013.01); *C12N 5/069* (2013.01); *C12N 2501/734* (2013.01); *C12N 2501/998* (2013.01)

(58) Field of Classification Search
None
See application file for complete search history.

(56) References Cited

U.S. PATENT DOCUMENTS

| | | | |
|---|---|---|---|
| 11,045,500 B2 * | 6/2021 | Levenberg .......... | A61L 27/3808 |
| 2004/0115176 A1 | 6/2004 | Swartz et al. | |
| 2007/0128171 A1 | 6/2007 | Tranquillo et al. | |

FOREIGN PATENT DOCUMENTS

| | | | |
|---|---|---|---|
| CN | 104371919 A | 2/2015 | |
| CN | 114591836 * | 6/2022 | |
| CN | 114591836 A | 6/2022 | |
| WO | WO-2005003317 A2 * | 1/2005 | ......... A61L 27/3808 |

OTHER PUBLICATIONS

King et al Cell Reports Methods 2, 100280, 1-12 (Year: 2022).*
Doung Tissue Engineering, 15(7), 1865-1876 (Year: 2009).*
Kaiser et al ACS Biomater. Sci. Eng. 5, 887-899 (Year: 2019).*
Gudapati et al Soft Matter, 16, 10506-10517 (Year: 2020).*
Twardowski Ann Biomed Eng. 42(5): 1074-1084 (Year: 2014).*
Li et al Signal Transduction and Targeted Therapy r: 152 (8), 1-29 (Year: 2023).*
Plecis et al Journal of Applied Physics, 104, 124909, 1-6 (Year: 2008).*
Su, Teng et al, Cardiac Stem Cell Patch Integrated with Microengineered Blood Vessels Promotes Cardiomyocyte Proliferation and Neovascularization after Acute Myocardial Infarction, ACS Applied Materials & Interfaces, 2018, 30 pages.
Su, Teng et al., Cardiac Stromal Cell Patch Integrated with Engineered Microvessels Improves Recovery from Myocardial Infarction in Rats and Pigs, ACS Biomaterials Science & Engineering, 2020, 22 pages.
Gudapati, Hemanth et al., Rheological Investigation of Collagen, Fibrinogen, and Thrombin Solutions for Drop-on-Demand 3D Bioprinting, Soft Matter, 2020, 42 pages.
International Search Report in PCT/CN2023/080957 mailed on Oct. 17, 2023, 8 pages.
Written Opinion in PCT/CN2023/080957 mailed on Oct. 17, 2023, 6 pages.
Oisin King et al., Functional Microvascularization of Human Myocardium in Vitro, Cell Reports Methods, 2022, 17 pages.
Nicholas J. Kaiser et al., Optimizing Blended Collagen-Fibrin Hydrogels for Cardiac Tissue Engineering with Human IPSC-Derived Cardiomyocyces, ACS Biomaterials Science & Engineering, 5: 887-899, 2019.
Guo, Haoyu et al., Recent Research Progress in Construction of Biomimetic Engineered Cardiac Tissue Based on Extracellular Matrix, Chinese Journal of Tissue Engineering Research, 25(10): 1577-1584, 2021.
First Office Action in Chinese Application No. 202310044224.1 mailed on Jan. 16, 2026, 19 pages.

* cited by examiner

*Primary Examiner* — Anoop K Singh
(74) *Attorney, Agent, or Firm* — PORUS IP LLC

(57) ABSTRACT

A method for preparing an engineered microvessel is provided. The method includes: obtaining a first dispersion by mixing a thrombin solution, a vascular endothelial cell suspension, a cardiomyocyte suspension, and a portion of a mixed culture medium, and obtaining a second dispersion by mixing a fibrinogen solution, a collagen solution, and another portion of the mixed culture medium, wherein the mixed culture medium includes a vascular endothelial cell culture medium and a cardiomyocyte culture medium; obtaining a gel pre-polymerisation solution by mixing the first dispersion and the second dispersion, and obtaining a cellular entity by curing the gel pre-polymerisation solution; and obtaining an engineered microvascular entity by placing the cellular entity in the mixed culture medium at a static status for static culture, and then placing the cellular entity in the mixed culture medium at a flowing status for dynamic culture.

4 Claims, 6 Drawing Sheets

METHODS FOR PREPARING ENGINEERED MICROVESSELS AND APPLICATIONS THEREOF

CROSS-REFERENCE TO RELATED APPLICATIONS

This application is a Continuation of International Application No. PCT/CN2023/080957, filed Mar. 11, 2023, which claims priority to Chinese Patent Application No. 202310044224.1, filed on Jan. 29, 2023, the entire contents of each of which are hereby incorporated by reference.

TECHNICAL FIELD

The present disclosure relates to the field of tissue engineering and biotechnology, and in particular, to a method for preparing an engineered microvessel and application thereof.

BACKGROUND

Currently, there are two main approaches to the preparation of engineered microvessels. The first approach involves using biological or polymer materials and techniques such as electrospinning and three-dimensional (3D) printing to create an engineered vessel with a tubular structure similar to a real blood vessel. While the engineered vessel is structurally similar to the real blood vessel, it differs significantly in physiological properties due to a lack of cellular attachment. For example, stiffness and elasticity of the engineered vessels differ greatly from stiffness and elasticity of the real blood vessel. Moreover, due to limitations in equipment precision, it is challenging to achieve a micro-scale inner diameter for the engineered microvessel. The second approach involves decellularization, where an engineered microvessel is obtained from a donor and then decellularized. However, the engineered vessel prepared through this approach is difficult to endothelialize.

Vascular endothelial cells can form a vascular lumen structure through a process referred to as sprouting. A density, a lumen size, and a length of the lumen structure are influenced by extracellular matrix, related growth factors (e.g., vascular endothelial growth factor (VEGF)), and physicochemical factors including mechanical regulation. However, a diameter of the self-formed vascular lumen structure by endothelial cells is too small, and the structure may collapse over time due to endothelial cell apoptosis, making it difficult to maintain the lumen structure for an extended period. Modifying cells and regulating physicochemical factors may aid in the formation, maintenance, and expansion of the lumen structure formed by endothelial cells. In particular, the regulation of mechanical factors such as tensile stress and shear stress may promote the formation of a rich microvascular network by endothelial cells, thus enhancing the occurrence, formation, and maintenance of the microvascular network to some extent. Nonetheless, the microvascular network has a relatively loose and fragile structure and does not possess the physiological characteristics of the microvessel.

Therefore, an improved method for preparing an engineered microvessel is urgently needed.

SUMMARY

One or more embodiments of the present disclosure provide a method for preparing an engineered microvessel. The method may include: obtaining a first dispersion by mixing a thrombin solution, a vascular endothelial cell suspension, a cardiomyocyte suspension, and a portion of a mixed culture medium, and obtaining a second dispersion by mixing a fibrinogen solution, a collagen solution, and another portion of the mixed culture medium, wherein the mixed culture medium includes a vascular endothelial cell culture medium and a cardiomyocyte culture medium; obtaining a gel pre-polymerisation solution by mixing the first dispersion and the second dispersion, and obtaining a cellular entity by curing the gel pre-polymerisation solution, wherein in the gel pre-polymerisation solution, a density of vascular endothelial cells is $1\times10^6$-$1\times10^7$ cell/mL, a density of cardiomyocytes is $5\times10^6$-$5\times10^7$ cell/mL, a concentration of fibrinogen is 2.5-10 mg/mL, a concentration of collagen is 0.1-0.5 mg/mL, and a concentration of thrombin is 1-10 U/mL; and obtaining an engineered microvessel entity by placing the cellular entity in the mixed culture medium at a static status for static culture, and then placing the cellular entity in the mixed culture medium at a flowing status for dynamic culture.

In some embodiments, the cardiomyocytes are one of mouse cardiomyocytes, rat cardiomyocytes, human embryonic stem cell-induced cardiomyocytes, or human pluripotent stem cell-induced cardiomyocytes. In some embodiments, the vascular endothelial cells are one of human umbilical vein endothelial cells, human arterial endothelial cells, human embryonic stem cells, or human pluripotent stem cell-induced endothelial cells. In some embodiments, the fibrinogen is bovine fibrinogen or human fibrinogen. In some embodiments, the collagen is Collagen, Type I, from rat tail or Collagen, Type IV, from rat tail.

In some embodiments, in the mixed culture medium, a volume ratio of the vascular endothelial cell culture medium to the cardiomyocyte culture medium is in a range of 1:1.5 to 1:2.

In some embodiments, the first dispersion further includes an auxiliary cell suspension; and in the gel pre-polymerisation solution, a count of auxiliary cells in the auxiliary cell suspension does not exceed 10% of a total count of cells.

In some embodiments, the auxiliary cells are one or more of adipocytes, fibroblasts, or smooth muscle cells.

In some embodiments, a temperature of the curing operation is in a range of 25° C.-37° C., and a duration of the curing operation is in a range of 10-30 minutes.

In some embodiments, during the static culture of the cellular entity placed in the mixing medium at the static status, the cellular entity is monitored in real time for culture according to a preset count of days of culture and a preset pulsation frequency. Within the preset count of days of culture of the cellular entity, if a pulsation frequency of the cellular entity is monitored to be less than the preset pulsation frequency, the cellular entity is placed in the mixed culture medium at the flowing status for dynamic culture. If the culture of the cellular entity exceeds the preset count of days of culture, the cellular entity is placed in the mixed culture medium at the flowing status for dynamic culture.

In some embodiments, the placing the cellular entity in the mixed culture medium at a static status for static culture includes: placing the cellular entity in a cell culture plate, and when the cellular entity has a spontaneous contractile and diastolic behavior, transferring the cellular entity to a flow chamber within a microfluidic chip for static culture.

In some embodiments, the placing the cellular entity in the mixed culture medium at a flowing status for dynamic culture includes: placing the cellular entity within a microfluidic chip and connecting the microfluidic chip to a perfusion device for dynamic culture of the cellular entity within the microfluidic chip. The perfusion device includes a first connecting tube, a second connecting tube, a pneumatic pump, and a container holding a culture medium. The microfluidic chip has a flow chamber with a single passageway, the flow chamber has an inlet and an outlet, the inlet of the flow chamber is connected to an outlet of the first connecting tube, the inlet of the first connecting tube is inserted into the culture medium within the container, the outlet of the flow chamber is connected to an inlet of the second connecting tube, an outlet of the second connecting tube is inserted into the container and located above the culture medium, and an outlet pipe of the pneumatic pump is inserted into the container and located above the culture medium.

One or more embodiments of the present disclosure provide an application of an engineered microvessel. An engineered microvessel entity obtained by the method described above is decellularized to obtain a cell-free engineered microvessel entity. Seed cells are then implanted into the cell-free engineered microvessel entity, and vascular endothelial cells are implanted in an inner wall of a microvascular lumen structure of the cell-free engineered microvessel entity. Depending on the type of the seed cells, static culture is carried out in a culture container followed by dynamic perfusion culture in a bioreactor. Ultimately, a vascularized engineered tissue matching the seed cells is obtained.

BRIEF DESCRIPTION OF THE DRAWINGS

The present disclosure will be further illustrated by way of exemplary embodiments, which will be described in detail through the accompanying drawings. These embodiments are not limiting, and in these embodiments the same numbering indicates the same structure, wherein.

Figure 1:
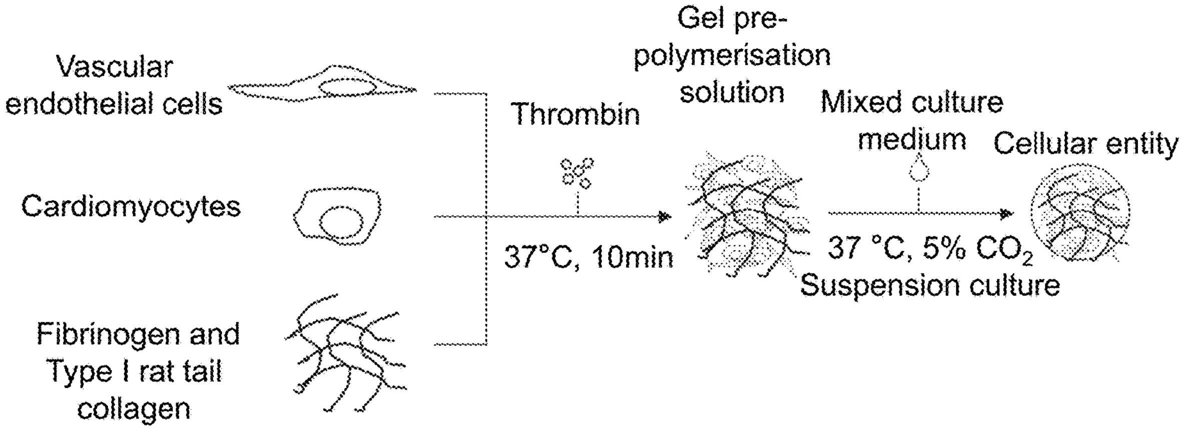
FIG. 1 is a flowchart of an exemplary process of a method for preparing an engineered microvessel according to some embodiments of the present disclosure.

Reference numerals in the drawings: 1 denotes a microfluidic chip, 2 denotes a first connecting tube, 3 denotes a second connecting tube, 4 denotes a pneumatic pump, 5 denotes a container, 11 denotes a flow chamber, 12 denotes an inlet of the flow chamber, 13 denotes an outlet of the flow chamber, 14 denotes a substrate, 15 denotes a negative mold, and 41 denotes an outlet pipe of the pneumatic pump.

DETAILED DESCRIPTION

In order to provide a clearer understanding of the technical solutions of the embodiments described in the present disclosure, a brief introduction to the drawings required in the description of the embodiments is given below. It is evident that the drawings described below are merely some examples or embodiments of the present disclosure, and for those skilled in the art, the present disclosure may be applied to other similar situations without exercising creative labor. Unless otherwise indicated or stated in the context, the same reference numerals in the drawings represent the same structures or operations.

It should be understood that, although the terms "first," "second," "third," etc., may be used in the present disclosure to describe various elements, these elements should not be limited by these terms. These terms are used solely to distinguish one element from another. For example, a first product may be referred to as a second product, and similarly, within the scope of exemplary embodiments of the present disclosure, the second product may be referred to as the first product.

As indicated in the present disclosure and in the claims, the singular forms "a," "an," and "the" may be intended to include the plural forms as well, unless the context clearly indicates otherwise. In general, the terms "comprise," "comprises," and/or "comprising," "include," "includes," and/or "including," when used in this disclosure, specify the presence of stated features, integers, steps, operations, elements, and/or components, but do not preclude the presence or addition of one or more other features, integers, steps, operations, elements, components, and/or groups thereof.

Unless otherwise defined, all technical and scientific terms used in the present disclosure have the same meaning as typically understood by those of ordinary skill in the art to which the present disclosure pertains.

FIG. 1 is a flowchart of an exemplary process of a method for preparing an engineered microvessel according to some embodiments of the present disclosure. The microvessel refers to a blood vessel with an inner diameter of 50 μm to 1 mm. As shown in FIG. 1, the method for preparing the engineered microvessel may include the following operations:

In S1, a first dispersion may be obtained by mixing a thrombin solution, a vascular endothelial cell suspension, a cardiomyocyte suspension, and a portion of a mixed culture medium, and a second dispersion may be obtained by mixing a fibrinogen solution, a collagen solution, and another portion of the mixed culture medium. The mixed culture medium includes a vascular endothelial cell culture medium and a cardiomyocyte culture medium. In some embodiments, the two portions of the mixed culture medium are identical in composition and/or volume.

Due to the presence of certain gel components in fibrinogen and collagen, if the cell suspension is mixed with fibrinogen and/or collagen first, it may cause uneven cell distribution. In addition, if thrombin and fibrinogen are mixed first, the thrombin and the fibrinogen may interact to coagulate quickly at a room temperature. Therefore, the cells are first dispersed in the thrombin solution (i.e., mixing the thrombin solution, the vascular endothelial cell suspension, the cardiomyocyte suspension, and the auxiliary cell suspension) before mixing the first dispersion with the second dispersion. This approach ensures more uniform cell distribution and prevents premature coagulation. Adding the mixed culture medium to both the first dispersion and the second dispersion helps enhance the activity of the cells (vascular endothelial cells and cardiomyocytes), thereby increasing the count, density, and inner diameter of generated vessels.

In some embodiments, the cardiomyocytes are one of mouse cardiomyocytes, rat cardiomyocytes, human embryonic stem cell-induced cardiomyocytes, or human pluripotent stem cell-induced cardiomyocytes. In some embodiments, the vascular endothelial cells are one of human umbilical vein endothelial cells, human arterial endothelial cells, human embryonic stem cells, or human pluripotent stem cell-induced endothelial cells. In some embodiments, the fibrinogen is bovine fibrinogen or human fibrinogen. In some embodiments, the collagen is Collagen, Type I, from rat tail or Collagen, Type IV, from rat tail.

In some embodiments, before performing operation S1, it is necessary to first prepare the fibrinogen solution, the collagen solution, and the thrombin solution, and to prepare the vascular endothelial cell suspension, the cardiomyocyte suspension, and the auxiliary cell suspension.

In some embodiments, a process for preparing the fibrinogen solution may include the following operations: a fibrinogen lyophilized powder may be preheated at 37° C. for 30 minutes, and a sodium chloride solution with a mass fraction of 0.9% may be preheated at 37° C. for 30 minutes. Then 20 mL of the preheated sodium chloride solution may be added slowly to 500 mg of the preheated fibrinogen lyophilized powder and placing the mixture in a water bath at 37° C. so that the fibrinogen lyophilized powder slowly dissolves into a fibrinogen solution with a concentration of 25 mg/mL. Finally, the fibrinogen solution may be dispensed and stored at a temperature of −20° C.

In some embodiments, a process for preparing the collagen solution may include the following operations: collagen powder may be dissolved in an acetic acid solution at 4° C. to obtain a 10 mg/mL collagen solution, and then the collagen solution may be diluted with 1×PBS phosphate-buffered saline to prepare collagen solutions of 3.5 mg/mL, 2 mg/mL, or 1 mg/mL, which may be then dispensed and stored at −20° C.

In some embodiments, a process for preparing the thrombin solution may include the following operations: 10 mL of a sodium chloride solution with a mass fraction of 0.9% may be slowly added to 1,000 U of thrombin powder, and the thrombin powder may be dissolved at a room temperature into a thrombin solution with a concentration of 100 U. Subsequently, the thrombin solution may be dispensed and stored at a temperature of −20° C.

In some embodiments, a process for preparing the vascular endothelial cell suspension may include the following operations: routine culture may be performed on primary vascular endothelial cells from human umbilical vein endothelial cells or human arterial endothelial cells using a specialized culture medium until the primary vascular endothelial cells reach the third generation and the third generation cells are cryopreserved. After the cryopreserved third generation cells are thawed, routine culture may be performed on the third generation cells in a culture flask, and the third generation cells may be digested when they reach 90% confluency on a bottom surface of the flask. Then the cells may be resuspended to obtain the vascular endothelial cell suspension. In this way, purification of the vascular endothelial cells is achieved, and the vascular endothelial cells in the obtained vascular endothelial cell suspension are fourth to sixth-generation vascular endothelial cells.

In some embodiments, a process for preparing the vascular endothelial cell suspension may further include the following operations: routine culture may be performed on human embryonic stem cell-induced endothelial cells or human pluripotent stem cell-induced endothelial cells in a culture plate. When the cells reach 90% confluency in the culture plate, the cells may be digested and resuspended to obtain the vascular endothelial cell suspension. The vascular endothelial cells in the obtained suspension are second to fourth-generation vascular endothelial cells.

In some embodiments, a process for preparing the cardiomyocyte suspension may include the following operations: primary cardiomyocytes from mouse cardiomyocytes or rat cardiomyocytes may be placed in a culture plate for routine incubation using DMEM/F12, 10% fetal bovine serum, and 1% double antibodies. When the primary cardiomyocytes adhere to a bottom surface of the culture plate and exhibit spontaneous pulsation, the primary cardiomyocytes may be digested and resuspended to obtain the cardiomyocyte suspension. In this way, purification of the cardiomyocytes is achieved, and the cardiomyocytes in the obtained cardiomyocyte suspension are first generation cardiomyocytes.

In some embodiments, a process for preparing the cardiomyocyte suspension may further include the following operations: maintenance culture may be performed on human embryonic stem cell-induced cardiomyocytes or human pluripotent stem cell-induced cardiomyocytes in a culture plate using a specialized culture medium. When the cardiomyocytes adhere to a bottom surface of the culture plate and exhibit spontaneous pulsation, the cardiomyocytes may be digested and resuspended to obtain the cardiomyocyte suspension. The cardiomyocytes in the obtained cardiomyocyte suspension are first generation cardiomyocytes.

In some embodiments, in the mixed culture medium, a volume ratio of the vascular endothelial cell culture medium to the cardiomyocyte culture medium is in a range of 1:1.5 to 1:2.

The vascular endothelial cell culture medium is a medium for culturing vascular endothelial cells, and the cardiomyocyte culture medium is a medium for culturing cardiomyocytes.

In some embodiments, in the mixed culture medium, a volume ratio of the vascular endothelial cell culture medium to the cardiomyocyte culture medium may be 1:2, 1:1.7, or 1:1.5

By configuring the volume ratio of the vascular endothelial cell culture medium to the cardiomyocyte culture medium to be in the range of 1:1.5 to 1:2, the mixed medium is more conducive to the activity of the vascular endothelial cells and the cardiomyocytes. Specifically, this configuration facilitates the formation of a vascular-like structure by the vascular endothelial cells, maintain stability of cardiomyocyte pulsation, and prolong the cardiomyocyte pulsation.

In some embodiments, the first dispersion may further include an auxiliary cell suspension.

The auxiliary cells are cells used to increase the activity of the vascular endothelial cells and the cardiomyocytes. In some embodiments, the auxiliary cells are one or more of adipocytes, fibroblasts, or smooth muscle cells.

In S2, a gel pre-polymerisation solution may be obtained by mixing the first dispersion and the second dispersion, and a cellular entity may be obtained by curing the gel pre-polymerisation solution. In the gel pre-polymerisation solution, a density of the vascular endothelial cells may be $1\times10^6$-$1\times10^7$ cell/mL, a density of the cardiomyocytes may be $5\times10^6$-$5\times10^7$ cell/mL, a concentration of the fibrinogen may be 2.5-10 mg/mL, a concentration of the collagen may be 0.1-0.5 mg/mL, and a concentration of the thrombin may be 1-10 U/mL.

In some embodiments, in the gel pre-polymerisation solution, the density of the vascular endothelial cells may be $5\times10^6$ cells/mL, the density of the cardiomyocytes may be $1\times10^7$ cells/mL, the concentration of the fibrinogen may be 5 mg/mL, the concentration of the collagen may be 0.2 mg/mL, and the concentration of the thrombin may be 3 U/mL.

In some embodiments, in the gel pre-polymerisation solution, the density of the vascular endothelial cells may be $2\times10^6$ cells/mL, the density of the cardiomyocytes may be $5\times10^6$ cells/mL, a density of primary human skin fibroblasts may be $5\times10^5$ cell/mL, the concentration of the fibrinogen may be 2.5 mg/mL, the concentration of the collagen may be 0.1 mg/mL, and the concentration of the thrombin may be 1 U/mL.

In some embodiments, in the gel pre-polymerisation solution, a count of the auxiliary cells in the auxiliary cell suspension may not exceed 10% of a total count of cells (i.e., the count of the auxiliary cells added to the extracellular matrix, excluding the vascular endothelial cells and the cardiomyocytes, may not exceed 10% of the total count of cells).

In the gel pre-polymerisation solution, the vascular endothelial cells can spontaneously generate a microvascular structure, the cardiomyocytes can spontaneously generate pulsation, and the auxiliary cells can maintain the activity of the vascular endothelial cells and the cardiomyocytes and delay an apoptotic time of the vascular endothelial cells and the cardiomyocytes. The role of the fibrinogen is to provide an extracellular matrix with a three-dimensional scaffolding structure required for the growth of seed cells. The role of the collagen is twofold: firstly, the collagen increases the initial activity of the vascular endothelial cells and the cardiomyocytes to enrich the initially generated microvascular structure; secondly, the collagen helps maintain the activity of vascular endothelial cells and the cardiomyocytes, and delay the apoptotic time of the vascular endothelial cells and the cardiomyocytes. The role of the thrombin is to interact with the fibrinogen to form a solid three-dimensional scaffolding material.

Figure 2:
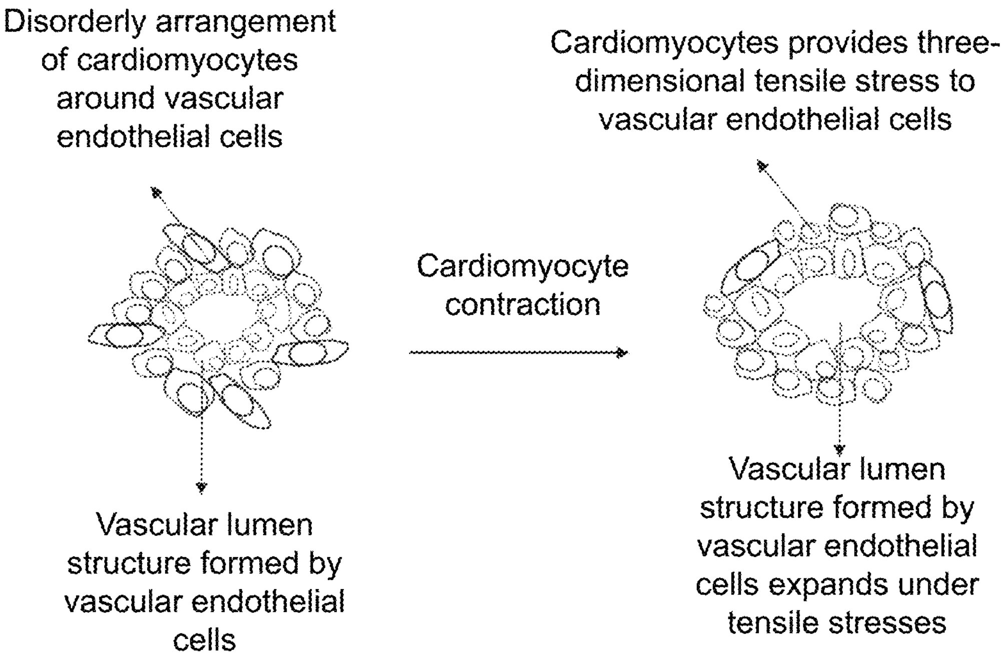
FIG. 2 is a schematic diagram illustrating spontaneous pulsating of cardiomyocytes in cellular entities acting on vascular endothelial cells according to some embodiments of the present disclosure.

In the gel pre-polymerisation solution formed by mixing the first dispersion and the second dispersion, the vascular endothelial cells and the cardiomyocytes are uniformly distributed. That is to say, the vascular endothelial cells are uniformly distributed around the vascular endothelial cells in the cellular entity. Since directions of tensile stresses generated by the pulsation of the uniformly distributed cardiomyocytes are random, the tensile stresses generated by the pulsation of the cardiomyocytes around the vascular endothelial cells may act on the vascular endothelial cells in three dimensions, which provides a physiological intensity at a stable frequency for the growth of the vascular endothelial cells (as shown in FIG. 2), thereby promoting the formation, expansion, and mutual fusion of the physiological microvascular lumen structure formed by the vascular endothelial cells. Experimental findings show that regulation of lumen structure formation by endothelial cells based on the three-dimensional tensile stress of cardiomyocytes is superior to spontaneous tube formation by endothelial cells. Furthermore, the physiological intensity of lumen structure formation regulation based on the three-dimensional tensile stress of cardiomyocytes is superior to that of regulation based on two-dimensional tensile stress generated by mechanical stretching.

In some embodiments, the curing operation may be performed in an incubator, a temperature of the curing operation may be in a range of 25° C.-37° C., and a duration of the curing operation may be in a range of 10-30 minutes. Performing the curing operation at a temperature within the above range may ensure cell activity.

In some embodiments, the temperature of the curing operation may be 37° C. and the duration of the curing operation may be 10 minutes.

In some embodiments, the temperature of the curing operation may be 37° C. and the duration of the curing operation may be 30 minutes.

In S3, an engineered microvessel entity may be obtained by placing the cellular entity in the mixed culture medium at a static status for static culture, and then placing the cellular entity in the mixed culture medium at a flowing status for dynamic culture.

Experimental findings suggest that a spontaneous pulsation force of cardiomyocytes weakens with time. Therefore, static culture is performed in an early stage and dynamic culture is performed through a fluid shear stress in a later stage to balance the weakened three-dimensional tensile stress, thereby maintaining the formed microvascular lumen structure, and promoting the further formation, expansion, and mutual fusion of the physiological microvascular lumen structure formed by the vascular endothelial cells, and ultimately forming a stable, non-collapsible, perfusable, micron-scale engineered vascular structure.

In some embodiments, during the static culture of the cellular entity placed in the mixing medium at the static status, the cellular entity may be monitored in real time for culture according to a preset count of days of culture and a preset pulsation frequency. Within the preset count of days of culture of the cellular entity, if a pulsation frequency of the cellular entity is monitored to be less than the preset pulsation frequency, the cellular entity may be placed in the mixed culture medium at the flowing status for dynamic culture.

In some embodiments, if the pulsation frequency of the cellular entity is not less than the preset pulsation frequency within the preset count of days of culture of the cellular entity, the cellular entity may be placed in the mixed culture medium at the flowing status for dynamic culture when the culture of the cellular entity exceeds the preset count of days of culture.

In some embodiments, the timing of the transition from the static culture to the dynamic culture may be regulated by setting the preset count of days of culture and the preset pulsation frequency, which visually reflect the activity of the cellular entity.

In some embodiments, the preset count of days of culture may be 6 to 8 days, and the preset pulsation frequency may be 28 to 35 beats/min. By regulating the timing of the transition from the static culture to the dynamic culture based on the preset count of days of culture and the preset pulsation frequency, when the cellular entity is cultured for the preset count of days of culture, the cellular entity forms a spherical structure, and a plurality of microvascular lumen structures with an inner diameter of several tens of micrometers may be formed inside the cellular entity. With the increase of culture time, the microvessels expand and fuse under the interaction of three-dimensional tensile stress generated by the spontaneous pulsation of the cardiomyocytes and the shear stress generated by the dynamic culture, resulting in the formation of a plurality of microvascular lumen structures with an inner diameter greater than one hundred micrometers inside the cell entity.

The engineered microvessel entity may be decellularized to obtain a cell-free engineered microvessel entity having a plurality of microvascular lumen (circular lumen) structures with an inner diameter ranging from 50 μm to 1 mm and a length of 500 μm or above. Testing of the cell-free engineered microvessel entity demonstrates that the microvascular lumen structures have a certain degree of stiffness, elasticity, and perfusability (i.e., the microvascular lumen structures have the physiological characteristics of in vivo microvessels).

In some embodiments, placing the cellular entity in the mixed culture medium at the static status for static culture may include: placing the cellular entity in a cell culture plate for static culture, and when the cellular entity has a spontaneous contractile and diastolic behavior, transferring the cellular entity to the mixed culture medium at the flowing status for dynamic culture.

In some embodiments, placing the cellular entity in the mixed culture medium at the flowing status for dynamic culture may include: placing the cellular entity in the flow chamber 11 within the microfluidic chip 1 for static culture and dynamic culture sequentially. After the static culture in the mixed culture medium at the static status is completed, the cellular entity may be transferred to the mixed culture medium at the flowing status for dynamic culture. Since the static culture and dynamic culture are not performed in the same cultivation device, the cellular entity may undergo an adaptation process after the transfer. Therefore, the dynamic culture in the mixed culture medium at the flowing status may include first performing static culture on the cell entity within the microfluidic chip 1 to allow the cell entity to adapt to the new culture environment, and then performing dynamic culture on the cell entity within the microfluidic chip 1. Experimental observations indicate that the duration of the static culture in the microfluidic chip 1 is approximately 1 to 2 days, after which the cell entity begins to exhibit the same pulsation frequency as in the static culture on the cell culture plate, indicating it is suitable to transition to the dynamic culture stage.

Figure 3:
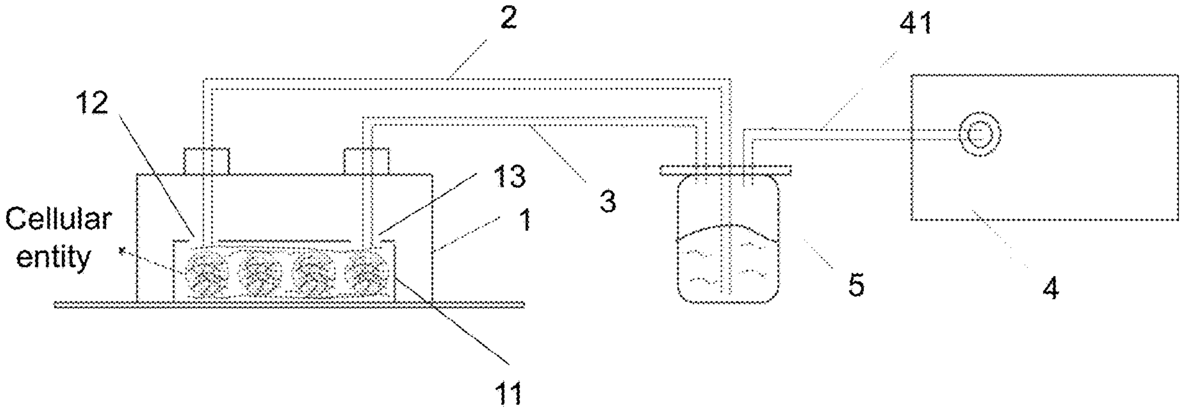
FIG. 3 is a schematic diagram of a structure of a perfusion device according to some embodiments of the present disclosure.

In some embodiments, the cellular entity may be placed within the microfluidic chip which is connected to a perfusion device for the dynamic culture of the cellular entity within the microfluidic chip. As shown in FIG. 3, the perfusion device includes a first connecting tube 2, a second connecting tube 3, a pneumatic pump 4, and a container 5 holding a culture medium. The microfluidic chip 1 has a flow chamber 11 with a single passageway, the flow chamber 11 has an inlet 12 and an outlet 13, the inlet 12 of the flow chamber 11 is connected to an outlet of the first connecting tube 2, the inlet of the first connecting tube 2 is inserted into the culture medium within the container 5, the outlet 13 of the flow chamber 11 is connected to an inlet of the second connecting tube 3, an outlet of the second connecting tube 3 is inserted into the container 5 and located above the culture medium, and an outlet pipe 41 of the pneumatic pump 4 is inserted into the container 5 and located above the culture medium. With the perfusion device set in this way, the pneumatic pump 4 may perfuse the culture medium into the flow chamber 11 of the microfluidic chip 1 at a certain speed, forming a stable fluid shear stress on an outer peripheral surface of the cellular entity.

Figure 4:
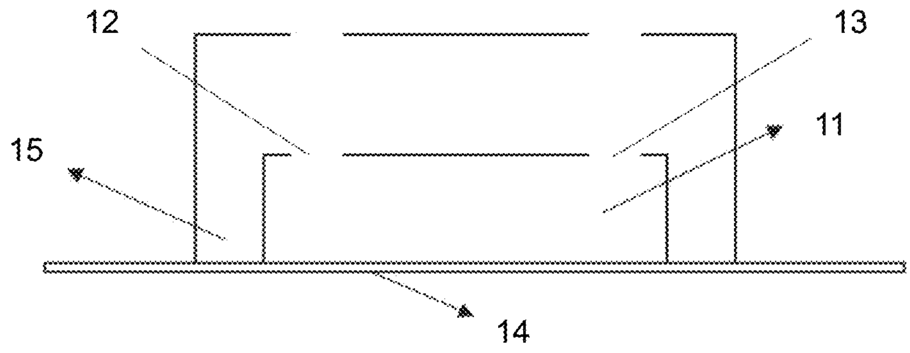
FIG. 4 is a schematic diagram of a structure of a microfluidic chip according to some embodiments of the present disclosure.

In some embodiments, as shown in FIG. 4, the microfluidic chip 1 includes a glass substrate 14 and a polydimethylsiloxane (PDMS) negative mold 15. The negative mold is provided with a groove, and two ends of a bottom of the groove are provided with a first through-hole and a second through-hole, respectively. The negative mold 15 is snapped onto the substrate 14, with a sealed connection between the negative mold 15 and the substrate 14, forming the flow chamber 11 between the groove and the substrate 14. The first through-hole and the second through-hole form the inlet 12 and the outlet 13 of the flow chamber 11, respectively. Preferably, the flow chamber 11 is rectangular shaped, with a length of 13-17 mm, a width of 8-12 mm, and a depth of 3-5 mm. The first through-hole and the second through-hole are circular, each has a diameter of 4-6 mm.

In some embodiments, the first connecting tube 2 and the second connecting tube 3 both have an inner diameter of 0.8-1 mm and an outer diameter of 1.5-1.7 mm. The pneumatic pump 4 may be a constant-flow syringe pump or a constant-pressure syringe pump.

In some embodiments, the pneumatic pump 4 performs a continuous perfusion of the mixed culture medium to the cellular entity within the microfluidic chip 1 at a flow velocity of 5-10 mm/s for more than three days, thereby ensuring that generated by the fluid flow within the microfluidic chip 1 further expands the microvascular lumen structure formed by the vascular endothelial cells within the cell entity and forms a microvascular structure with certain rigidity.

The present disclosure also provides an application of an engineered microvessel. An engineered microvessel entity obtained by the method described above is decellularized to obtain a cell-free engineered microvessel entity. Seed cells are then implanted into the cell-free engineered microvessel entity, and vascular endothelial cells are implanted in an inner wall of the microvascular lumen structure of the cell-free engineered microvessel entity. Depending on the type of the seed cells, static culture is carried out in a culture container followed by dynamic perfusion culture in a bioreactor. Ultimately, a vascularized engineered tissue compatible with the seed cells is obtained.

The beneficial effects of the embodiments of the present disclosure include, but are not limited to: (1) The embodiments of the present disclosure utilize the spontaneous pulsation of cardiomyocytes to generate the three-dimensional physiological tensile stress through rhythmic contraction and relaxation, replacing the two-dimensional tensile stress formed by mechanical stretching. Combining the three-dimensional physiological tensile stress with the fluid shear stress, the method regulates the vascular endothelial cells that can uniformly mix with cardiomyocytes, thereby authentically simulating a mechanical environment of microvascular growth in vivo and forming an engineered microvascular structure different from the spontaneous tube formation of vascular endothelial cells. (2) The engineered microvascular structure provided by the embodiments of the present disclosure has certain rigidity and elasticity, can be perfused (i.e., possesses physiological characteristics of microvessels), and does not shrink or collapse with the apoptosis of vascular endothelial cells. The engineered microvascular structure can maintain a circular lumen structure for a long time in vitro, and after decellularization, a cell-free engineered microvessel can be obtained. (3) It is the first time in this field to combine the physiological three-dimensional tensile stress and the fluid shear stress to jointly regulate the behavior of the vascular endothelial cells, so as to promote the further expansion and mutual fusion of the lumen structure formed by the vascular endothelial cells. (4) The engineered microvessels prepared in the embodiments of the present disclosure can be used for tissue engineering construction and tissue repair (i.e., by re-implantation of cells, other seed cells are implanted in the decellularized engineered microvessel entity, and the lumen structure therein can be vascularized by re-endothelialization, and finally a vascularized engineered tissues closer to the natural tissue is formed). (5) The entire process of the embodiments of the present disclosure is technically simple to achieve, has low preparation costs, does not involve other scaffold materials or high-end mechanical equipment, and the final products can be widely applied in the field of tissue engineering.

The experimental techniques in the following Embodiments, unless otherwise specified, are conventional techniques. The test materials used in the following Embodiments, unless otherwise specified, are obtained from standard biochemical reagent companies. Quantitative assays in the following Embodiments are performed with three replicate experiments, and the results are averaged.

EMBODIMENTS

Embodiment 1

An engineered microvessel was prepared using a method including the following operations:

In A1, 25 mg/mL fibrinogen solution, Type I rat tail collagen solution, 100 U thrombin solution, a human umbilical vein endothelial cell (HUVEC) suspension, and a human pluripotent stem cell-induced cardiomyocyte (hiPSC-CM) suspension were prepared.

In A2, a first dispersion was obtained by mixing the 100 U thrombin solution, the HUVEC suspension, the hiPSC-CM suspension, and a portion of a mixed culture medium, and a second dispersion was obtained by mixing the 25 mg/mL fibrinogen solution, the collagen solution, and another portion of the mixed culture medium.

In A3, the first dispersion and the second dispersion were mixed on crushed ice to obtain 1 mL of gel pre-polymerisation solution, and 400 uL of the gel pre-polymerisation solution was added to a 1 mL centrifuge tube and placed in an incubator with 5% $CO_2$ at 37° C. for 10 min for a curing operation to obtain a cellular entity. In the gel pre-polymerisation solution, a density of HUVECs was $5\times10^6$ cells/mL, a density of hiPSC-CMs was $1\times10^7$ cells/mL, a concentration of fibrinogen was 5 mg/mL, a concentration of Type I rat tail collagen was 0.2 mg/mL, and a concentration of thrombin was 3 U/mL. A total amount of gel pre-polymerisation solution may be increased or decreased proportionally according to a count of the engineered microvessels to be prepared.

Figure 5:
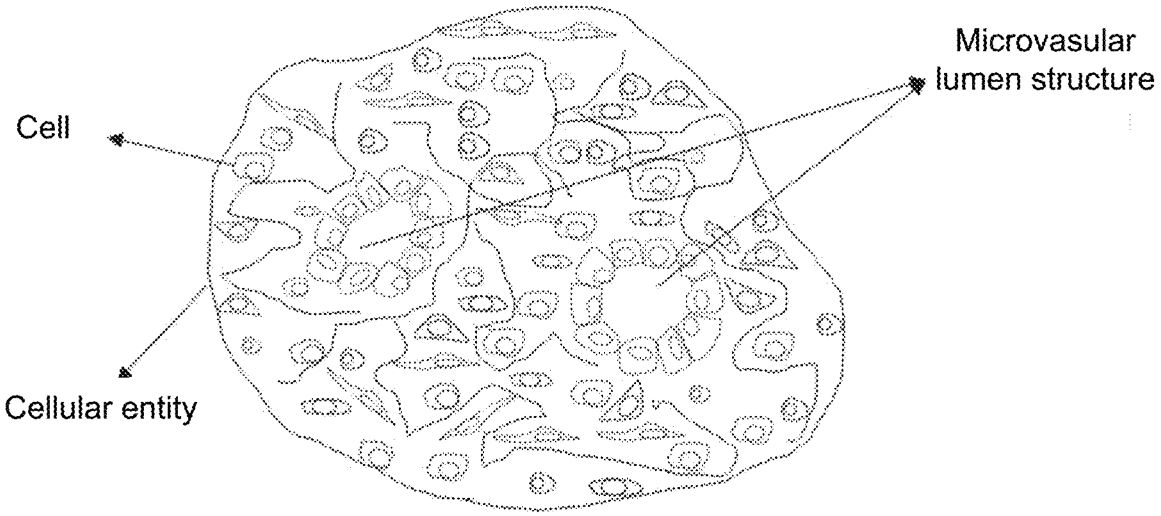
FIG. 5 is a schematic diagram of a cross-sectional structure of an engineered microvessel entity according to Embodiment 1 of the present disclosure.

In A4: the cellular entity was placed in a 24-well plate, a mixed culture medium was added to the 24-well plate, and placed into an incubator with 5% $CO_2$ at 37° C. for suspension culture. A fresh mixed culture medium was replaced every other day, and the spontaneous pulsation of the cellular entity, which was produced by the hiPSC-CMs, may be observed under a microscope after two days of culture. Subsequently, the cellular entity was transferred to a flow chamber within a microfluidic chip and placed in an incubator with 5% $CO_2$ at 37° C. for culture. During this process, vascular endothelial cells spontaneously formed abundant lumen structures within the cellular entity, and when a pulsation frequency of the cellular entity was monitored to be less than 30 beats/min after six days of static culture, the microfluidic chip was installed into a perfusion device. A constant-flow syringe pump was used to continuously perfuse the cellular entity in the microfluidic chip with mixed culture medium at a flow velocity of 5 mm/s for eight days to obtain an engineered microvessel entity as shown in FIG. 5.

During the static culture, the microfluidic chip was placed in a petri dish to which a mixed culture medium was added, and the mixed culture medium completely covered an inlet and an outlet of the flow chamber of the microfluidic chip. The mixed medium was prepared by mixing EGM-2 medium (endothelial cell medium) and hiPSC-CM medium (cardiomyocyte medium) at a volume ratio of 1:2.

The microvessels in the engineered microvessel entity obtained by the method have microvascular physiological characteristics, i.e., the microvessels have a certain degree of stiffness and elasticity and can be perfused.

Figure 6:
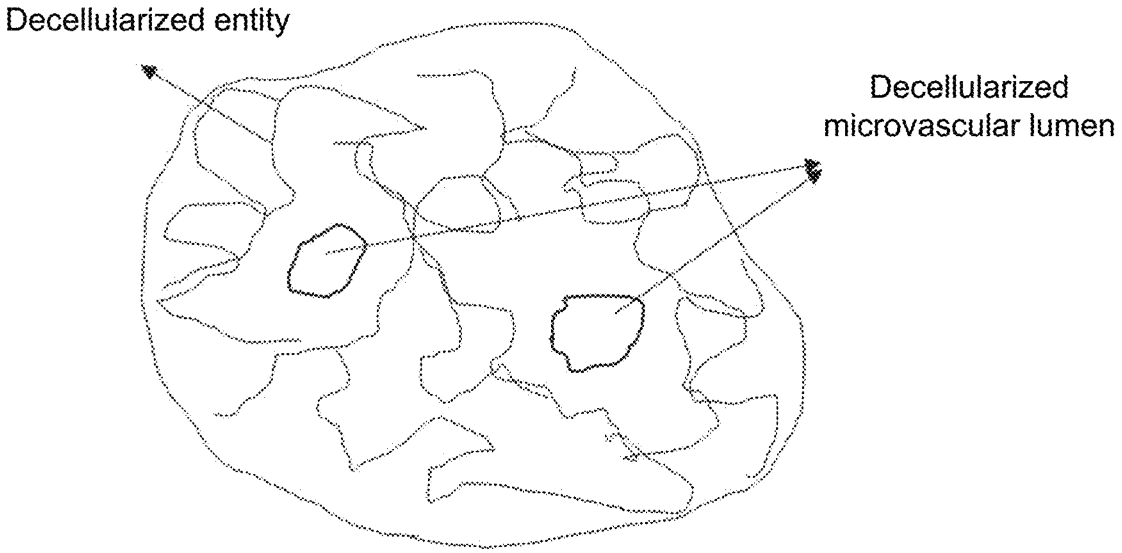
FIG. 6 is a schematic diagram of a cross-sectional structure of a cell-free engineered microvessel entity according to Embodiment 1 of the present disclosure.

The engineered microvessel entity obtained was decellularized to obtain a cell-free engineered microvessel entity, as shown in FIG. 6. Islet cells were implanted into the cell-free engineered microvessel entity, and then vascular endothelial cells were implanted on inner walls of decellularized microvascular lumens of the cell-free engineered microvessel entity. Static culture and dynamic culture were performed to obtain a vascularised engineered tissue compatible with the islet cells.

Embodiment 2

An engineered microvessel was prepared using a method including the following operations:

In A1, 25 mg/mL fibrinogen solution, Type I rat tail collagen solution, 100 U thrombin solution, a human umbilical vein endothelial cell (HUVEC) suspension, and a human pluripotent stem cell-induced cardiomyocyte (hiPSC-CM) suspension were prepared.

In A2, a first dispersion was obtained by mixing the 100 U thrombin solution, the HUVEC suspension, the hiPSC-CM suspension, and a portion of a mixed culture medium, and a second dispersion was obtained by mixing the 25 mg/mL fibrinogen solution, the collagen solution, and another portion of the mixed culture medium.

In A3, the first dispersion and the second dispersion were mixed on crushed ice to obtain 1 mL of gel pre-polymerisation solution, and 400 uL of the gel pre-polymerisation solution was added to a 1 mL centrifuge tube and placed in an incubator with 5% $CO_2$ at 37° C. for 10 min for a curing operation to obtain a cellular entity. In the gel pre-polymerisation solution, a density of HUVECs was $5\times10^6$ cells/mL, a density of hiPSC-CMs was $1\times10^7$ cells/mL, a concentration of fibrinogen was 5 mg/mL, a concentration of Type I rat tail collagen was 0.2 mg/mL, and a concentration of thrombin was 3 U/mL. A total amount of gel pre-polymerisation solution may be increased or decreased proportionally according to a count of the engineered microvessels to be prepared.

In A4, the cellular entity was placed in a 24-well plate, a mixed culture medium was added to the 24-well plate and placed into an incubator with 5% $CO_2$ at 37° C. for suspension culture. A fresh mixed culture medium was replaced every other day, and the spontaneous pulsation of the cellular entity, which was produced by the hiPSC-CMs, was observed under a microscope after two days of culture. Subsequently, the cellular entity was transferred to a flow chamber within a microfluidic chip and placed in an incubator with 5% $CO_2$ at 37° C. for culture. During this process, vascular endothelial cells spontaneously formed abundant lumen structures within the cellular entity, and when a pulsation frequency of the cellular entity was monitored to be still greater than 30 beats/min after eight days of static culture, the microfluidic chip was installed into a perfusion device. A constant-flow syringe pump was used to continuously perfuse the cellular entity in the microfluidic chip with mixed culture medium at a flow velocity of 5 mm/s for three days to obtain an engineered microvessel entity.

During the static culture, the microfluidic chip was placed in a petri dish to which a mixed culture medium was added, and the mixed culture medium completely covered an inlet and an outlet of the flow chamber of the microfluidic chip. The mixed medium was prepared by mixing EGM-2 medium (endothelial cell medium) and hiPSC-CM medium (cardiomyocyte medium) at a volume ratio of 1:1.7.

The microvessels in the engineered microvessel entity obtained by the method have microvascular physiological characteristics, i.e., the microvessels have a certain degree of stiffness and elasticity and can be perfused.

The engineered microvessel entity obtained was decellularized to obtain a cell-free engineered microvessel entity. Islet cells were implanted into the cell-free engineered microvessel entity, and then vascular endothelial cells were implanted on inner walls of decellularized microvascular lumens of the cell-free engineered microvessel entity. Static culture and dynamic culture were performed to obtain a vascularised engineered tissue compatible with the islet cells.

Embodiment 3

An engineered microvessel was prepared using a method including the following operations:

In A1, 25 mg/mL fibrinogen solution, Type I rat tail collagen solution, 100 U thrombin solution, a human umbilical vein endothelial cell (HUVEC) suspension, a human pluripotent stem cell-induced cardiomyocyte (hiPSC-CM) suspension, and a primary human skin fibroblast suspension were prepared.

In A2, a first dispersion was obtained by mixing the 100 U thrombin solution, the HUVEC suspension, the hiPSC-CM suspension, the primary human skin fibroblast suspension, and a portion of a mixed culture medium, and a second dispersion was obtained by mixing the 25 mg/mL fibrinogen solution, the collagen solution, and another portion of the mixed culture medium.

In A3, the first dispersion and the second dispersion were mixed on crushed ice to obtain 1 mL of gel pre-polymerisation solution, and 400 uL of the gel pre-polymerisation solution was added to a 1 mL centrifuge tube and placed in an incubator with 5% $CO_2$ at 37° C. for 10 min for a curing operation to obtain a cellular entity. In the gel pre-polymerisation solution, a density of HUVECs was $2\times10^6$ cells/mL, a density of hiPSC-CMs was $5\times10^6$ cells/mL, a density of primary human skin fibroblasts was $5\times10^5$ cell/mL, a concentration of fibrinogen was 2.5 mg/mL, a concentration of Type I rat tail collagen was 0.1 mg/mL, and a concentration of thrombin was 1 U/mL. A total amount of gel pre-polymerisation solution may be increased or decreased proportionally according to a count of the engineered microvessels to be prepared.

In A4, the cellular entity was placed in a 24-well plate, a mixed culture medium was added to the 24-well plate and placed into an incubator with 5% $CO_2$ at 37° C. for suspension culture. A fresh mixed culture medium was replaced every other day, and the spontaneous pulsation of the cellular entity, which was produced by the hiPSC-CMs, was observed under a microscope after two days of culture. Subsequently, the cellular entity was transferred to a flow chamber within a microfluidic chip and placed in an incubator with 5% $CO_2$ at 37° C. for culture. During this process, vascular endothelial cells spontaneously formed abundant lumen structures within the cellular entity, and when a pulsation frequency of the cellular entity was monitored to be less than 30 beats/min after three days of static culture, the microfluidic chip was installed into a perfusion device. A constant-flow syringe pump was used to continuously perfuse the cellular entity in the microfluidic chip with mixed culture medium at a flow velocity of 5 mm/s for seven days to obtain an engineered microvessel entity.

During the static culture, the microfluidic chip was placed in a petri dish to which a mixed culture medium was added, and the mixed culture medium completely covered an inlet and an outlet of the flow chamber of the microfluidic chip. The mixed medium was prepared by mixing EGM-2 medium (endothelial cell medium) and hiPSC-CM medium (cardiomyocyte medium) at a volume ratio of 1:1.5.

The microvessels in the engineered microvessel entity obtained by the method have microvascular physiological characteristics, i.e., the microvessels have a certain degree of stiffness and elasticity and can be perfused.

The engineered microvessel entity obtained was decellularized to obtain a cell-free engineered microvessel entity, as shown in FIG. 6. Islet cells were implanted into the cell-free engineered microvessel entity, and then vascular endothelial cells were implanted on inner walls of decellularized microvascular lumens of the cell-free engineered microvessel entity. Static culture and dynamic culture were performed to obtain vascularised engineered tissues compatible with the islet cells.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures, or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

It should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This way of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the present disclosure are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameter set forth in the written description and attached claims are approximations that may vary depending upon the desired properties sought to be obtained by a particular embodiment. In some embodiments, the numerical parameter should be construed in light of the number of reported significant digits and by applying ordinary rounding techniques. Notwithstanding that the numerical ranges and parameter setting forth the broad scope of some embodiments of the present disclosure are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the present disclosure disclosed herein are illustrating of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A method for preparing an engineered microvessel entity, the method comprising:

(i) mixing a thrombin solution, a vascular endothelial cell suspension, a cardiomyocyte suspension, and a portion of a mixed culture medium to obtain a first dispersion, and mixing a fibrinogen solution, a collagen solution, and another portion of the mixed culture medium to obtain a second dispersion, wherein the mixed culture medium comprises a vascular endothelial cell culture medium and a cardiomyocyte culture medium in a volume ratio of 1:1.5 to 1:2;

(ii) mixing the first dispersion and the second dispersion to obtain a gel pre-polymerization solution comprising $1\times10^6$-$1\times10^7$ cell/mL of vascular endothelial cells, $5\times10^6$-$5\times10^7$ cell/mL of cardiomyocytes, 0.1-0.5 mg/mL of collagen, 2.5-10 mg/mL of fibrinogen, and 1-10 U/mL of thrombin, (iii) curing the gel pre-polymerization solution at a temperature of 25° C.-37° C. for 10-30 minutes to form a cellular entity, (iv) placing the cellular entity from (iii) in the mixed culture medium at a static status with a flow velocity of 0 mm/s for static culture for 6-8 days to obtain a cellular entity with a preset pulsation frequency of 28-35 beats/min, and (v) placing the cellular entity with a preset pulsation frequency of 28-35 beats/min from (iv) in the mixed culture medium at a flowing status with a flow velocity of 5-10 mm/s in dynamic culture to obtain an engineered microvessel entity, wherein the engineered microvessel entity comprises a plurality of microvascular lumen structures with an inner diameter ranging from 500 μm to 1 mm, and the plurality of microvascular lumen structures that are stable, non-collapsible, and perfusable.

2. The method of claim 1, wherein the cardiomyocytes is selected from a group consisting of mouse cardiomyocytes, rat cardiomyocytes, and cardiomyocytes obtained from human pluripotent stem cell; the vascular endothelial cells is selected from a group consisting of human umbilical vein endothelial cells, human arterial endothelial cells, and endothelial cells obtained from human pluripotent stem cell; the fibrinogen is bovine fibrinogen or human fibrinogen; and the collagen is Collagen Type I obtained from rat tail or Collagen Type IV obtained from rat tail.

3. The method of claim 1, wherein the placing the cellular entity in the mixed culture medium at a static status for static culture includes:

placing the cellular entity in a cell culture plate, and transferring the cellular entity to a flow chamber within a microfluidic chip for static culture after the cellular entity has a spontaneous contractile and diastolic behavior.

4. The method of claim 1, wherein the placing the cellular entity in the mixed culture medium at a flowing status for dynamic culture includes:

placing the cellular entity within a microfluidic chip and connecting the microfluidic chip to a perfusion device for dynamic culture of the cellular entity within the microfluidic chip.

* * * * *